United States Patent [19]

Illy

[11] 4,126,590
[45] Nov. 21, 1978

[54] SULPHONYLTETRAZOLES AS CHEMICAL BLOWING AGENTS

[75] Inventor: Hugo Illy, Reinach, Switzerland

[73] Assignee: Ciba-Geigy Corporation, Ardsley, N.Y.

[21] Appl. No.: 846,286

[22] Filed: Oct. 28, 1977

[30] Foreign Application Priority Data

Nov. 5, 1976 [CH] Switzerland ............... 13967/76

[51] Int. Cl.² ............................................. C08J 9/10
[52] U.S. Cl. ..................................... 521/89; 521/180; 521/182; 521/143
[58] Field of Search ............ 260/2.5 N, 2.5 R, 308 D, 260/2.5 HA, 2.5 HB

[56] References Cited

U.S. PATENT DOCUMENTS 3,442,829  5/1969  Moore et al. ................. 260/2.5 HA
3,873,477  3/1975  Beck et al. .................... 260/2.5 HA Primary Examiner—Morton Foelak
Attorney, Agent, or Firm—Luther A. R Hall

[57] ABSTRACT

Sulfonyltetrazoles of formula I,

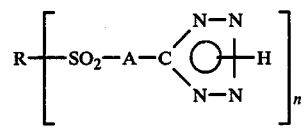

wherein $n$ is 1 or 2, A is alkylene and R is a mono- or divalent hydrocarbon residue, are usable as blowing agents for thermoplastic polymers. These compounds decompose at temperatures above 200° C, therefore they can be used preferably for foaming thermoplasts of higher softening temperature such as aromatic polycarbonates, polyesters or polyethers.

5 Claims, No Drawings

SULPHONYLTETRAZOLES AS CHEMICAL BLOWING AGENTS

The invention relates to a process for foaming thermoplastic materials (thermoplasts) by adding chemical blowing agents which decompose when heated and give off gas.

The production of foamed moulded shapes from thermoplastics by the addition of chemical blowing agents in the moulding process, for example during injection moulding or extrusion, has been known for a long time. The decomposition of the blowing agent occurs in the plasticised thermoplastic material, and the decomposition temperature should be between the softening temperature of the thermoplastic material and the maximum processing temperature. The decomposition temperature of the blowing agent should preferably be about 20° C. below the maximum processing temperature in order to obtain a homogeneous cellular structure and maximum utilisation of the blowing agent.

The decomposition of the blowing agent has therefore to occur within a relatively narrow temperature range. The gas formed on decomposition should be odorless and inert. The blowing agent should break down completely into gaseous decomposition products, or alternatively the non-gaseous decomposition products should be soluble in the plastics material, and must not lead to discoloration or to changes in the physical or chemical properties of the plastics material.

The blowing agents hitherto known do not in most cases satisfy all these requirements, and are therefore suitable mainly only for specific fields of application. Thus, for example, organic hydrazides and semicarbazides split off ammonia, as a result of which polyesters or polycarbonates can be ammonolytically broken down. The known azodicarbonamide forms solid decomposition residues which are insoluble in the customary thermoplasts. Its use moreover is associated with a considerable smell contamination during foaming. 5-Phenyl-tetrazole has already been suggested as a blowing agent, especially for the foaming of thermoplasts having relatively high processing temperatures. This blowing agent does not result in the formation of residues, but produces a gas yield lower than that of azodicarbonamide.

It was the object of the invention to find for the foaming of thermoplastic materials chemical blowing agents which do not have the disadvantages described above, particularly the disadvantages of causing discoloration and creating a smell nuisance.

It has been found that sulphonyltetrazoles of the formula I

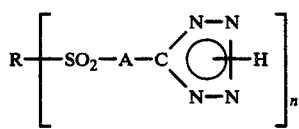

wherein
$n$ is 1 or 2,
A represents an alkylene group which has 1-5 C atoms and which can be substituted by phenyl, and
R represents, if $n$ is 1, alkyl having 1-4 C atoms, cyclohexyl, phenylalkyl having 7-8 C atoms, or an aryl group which has 6-10 C atoms and which can be substituted by alkyl having 1-2 C atoms, alkoxy having 1-2 C atoms, halogen, acylamino having 2-3 C atoms, carboxy or alkoxycarbonyl having 2-3 C atoms, and, if $n$ is 2, represents phenylene, naphthylene or a radical of the formula II

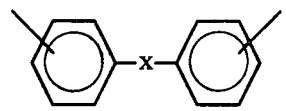

wherein X can be a direct bond, —O—, —S—, —SO$_2$—, —CH$_2$—, —C(CH$_3$)$_2$— or —NH—, are advantageously suitable as blowing agents for the foaming of thermoplastic materials.

In this formula, A can represent a straight-chain or branched-chain alkylene group which has 1-5 C atoms and which can be substituted by phenyl, such as —CH$_2$—, —CH$_2$—CH$_2$—, —CH(CH$_3$)—, —CH$_2$—CH(CH$_3$)— or —CH$_2$—CH(C$_6$H$_5$)—CH$_2$—.

As a monovalent radical, R can represent, for example, methyl, ethyl, propyl, butyl, cyclohexyl, benzyl, phenylethyl, phenyl, naphthyl, tolyl, xylyl, methoxyphenyl, ethoxyphenyl, chlorophenyl, bromophenyl, difluorophenyl, 4-acetylaminophenyl, 3-propionylaminophenyl, 3-carboxyphenyl, 3-methoxycarbonylphenyl or 4-isopropoxycarbonylphenyl.

As a bivalent radical, R can represent, for example, 1,3-phenylene, 1,6-naphthylene, or a bivalent radical of diphenylmethane, diphenyl ether, diphenylsulphide, diphenylsulphone, diphenylamine or 2,2-diphenylpropane.

The sulphonyltetrazoles preferably used are those of formula I wherein $n$ is 1, A represents a methylene group or ethylene group, and R represents phenyl, tolyl or methyl. The compounds concerned are 5-phenylsulphonylmethyl-tetrazole, 5-phenylsulphonylethyl-tetrazole, 5-methylsulphonylethyltetrazole and 5-methylsulphonylmethyl-tetrazole, and of these the last-mentioned in particular is distinguished by a high gas yield. Thus, for example, the gas yield on heating 5-methylsulphonylmethyl-tetrazole without plastics material to 300° C. is 280 ml/g. In comparison to this, the gas yield from 5-phenyltetrazole under the same conditions is 180 ml/g. A further advantage of the sulphonyltetrazoles according to the invention is that even at high foaming temperatures they cause no noticeable discoloration of the substrate and no smell contamination.

The sulphonyltetrazoles of the formula I can be produced, using methods known per se, by reaction of nitriles with hydrazoic acid or with salts thereof, e.g. by the reaction of nitriles with inorganic azides in polar solvents, described in J. Amer. Chem. Soc. 80, 3908 (1958). In the case in question the corresponding sulphonylalkyl nitriles of the formula III are reacted according to the following reaction pattern:

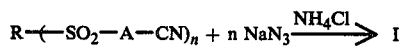

III

The nitriles of the formula III can be obtained for example by reaction of a sulphinic acid of the formula R—(SO$_2$H)$_n$, or a salt thereof, with chloroacetonitrile, chloropropionitrile, acrylonitrile or methacrylonitrile. Other methods of producing the nitriles of the formula III are the oxidation of the corresponding thionitriles R-(-S—A—CN)$_n$ or the dehydration of the corresponding amides of the formula R-(-SO$_2$—A—CONH$_2$)$_n$, e.g. by means of phosphorus pentoxide.

Some of the tetrazoles usable according to the invention are already known compounds. In J. Med. Chem. 12, 550 (1969) are thus described 5-isopropylsulphonyl-methyl-tetrazole, 5-(p-chlorophenylsulphonyl)-methyl-tetrazole and 5-(p-tolylsulphonyl)-methyl-tetrazole.

Furthermore, 5-(phenylsulphonylmethyl)-tetrazole is mentioned in the Russian journal Khim.Getrocikl.Soedinenja 1974, No. 12, 1626-1628.

There has however hitherto been no mention anywhere of the use of these compounds as chemical blowing agents.

The invention therefore relates also to the compounds of the formula I

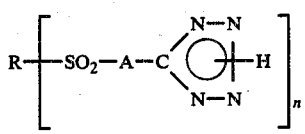

wherein
$n$ is 1 or 2,
A represents an alkylene group having 1-3 C atoms, and
R represents, if $n$ is 1, alkyl having 1-4 C atoms, cyclohexyl, phenylalkyl having 7-8 C atoms, or an aryl group which has 6-10 C atoms and which can be substituted by alkyl having 1-2 C atoms, alkoxy having 1-2 C atoms, halogen, acylamino having 2-3 C atoms, carboxy or alkoxycarbonyl having 2-3 C atoms, and, if $n$ is 2, represents phenylene, naphthylene, or a radical of the formula II

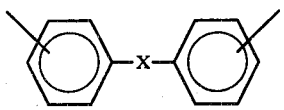

wherein X can be a direct bond, —O—, —S—, —SO$_2$—, —CH$_2$—, —C(CH$_3$)$_2$— or —NH—, with the exception of the already known compounds mentioned in the foregoing.

The decomposition temperature of the sulphonyltetrazoles of the formula I depends on the substituent R as well as on the nature of the alkylene group A.

Thermoplastic materials (thermoplasts) which can be foamed according to the invention are, for example, polyolefins such as polyethylene or polypropylene, polystyrene and styrene copolymers such as IPS or ABS polymers, polyvinyl chloride, polyacetals, polycarbonates, aromatic polyethers, polysulphones and polysulphone ethers, polyesters such as polyethylene or polybutyleneterephthalate, polyamides such as polycaprolactam, and also mixtures of such polymers. Since the decomposition temperature of the bis-tetrazoles of the formula I can be varied within certain limits by the choice of R and A, plastics having different processing temperatures can be foamed. In this manner, the sulphonyltetrazoles of the formula I are suitable for foaming at temperatures from 200° to above 300° C., preferably between 230° and 300° C. The process according to the invention is therefore suitable preferably for the foaming of polypropylene, styrene copolymers, polycarbonates, aromatic polyethers and polyether sulphones, polyesters and polyamides.

The addition of the blowing agents to the plastics can be made by dry mixing, with preferably an adhesive being added. The adhesives used can be, for example, long-chain fatty acids or salts thereof, esters or amides. The blowing agents can also be added in the dissolved form, or in the form of a masterbatch. What generally applies is that the more uniformly the blowing agent is mixed with the plastics material, the more finely porous and homogeneous the foam becomes.

The foaming of the mixture of the thermoplast and blowing agent is effected by known processes comprising heating with simultaneous moulding. The most important methods are injection moulding and extrusion.

The amount of blowing agent added depends in the first place on the degree of foaming required; it depends also on the respective gas yield from the blowing agent employed. In general, 0.05 to 5% by weight of blowing agent, preferably 0.1 to 2% by weight, is used.

The plastics used can contain additives such as those customary in plastics technology, such as fillers and reinforcing agents, glass fibres, pigments, lubricants, stabilisers, antistatic agents, nucleation agents, flame-proofing agents, plasticisers, emulsifiers or optical brighteners. Such additives can be added simultaneously with the blowing agents.

The Examples which follow illustrate the production and use of the sulphonyltetrazoles of the formula I. Except where otherwise stated, 'parts' denote parts by weight, temperatures are given in degrees Centigrade, and percentages are percent by weight.

EXAMPLE 1

5-(p-Tolylsulphonyl-methyl)-tetrazole 97.5 parts of p-tolylsulphonyl-acetonitrile are stirred together with 39 parts of sodium azide, 32 parts of ammonium chloride and 200 parts of dimethylformamide for 10 hours at 120°–130° C. The dimethylformamide is distilled off in vacuo, and the residue is dissolved in 1000 parts of water with the addition of sodium hydroxide to give pH 9. The solution is treated with animal charcoal, and precipitation is effected at pH 2-3 by the addition of hydrochloric acid. Recrystallisation of the precipitate from isopropanol yields 85 parts of 5-(p-tolylsulphonylmethyl)-tetrazole in the form of white crystals which melt at 206°–208°.

EXAMPLE 2

5-(Methylsulphonyl-methyl)-tetrazole 53.5 parts of methylsulphonylacetonitrile, 32 parts of sodium azide, 29 parts of ammonium chloride and 200 parts of dimethylformamide are stirred at 130° C. for 12 hours, and then treated as in Example 1. The alkaline solution clarified with animal charcoal is shaken with ether, and hydrochloric acid is added to the aqueous phase, whereupon the product precipitates in the form of white crystals. Recrystallisation from isopropanol yields 44 parts, which melt at 183°–185°.

EXAMPLE 3

5-[2-(Phenylsulphonyl)ethyl]-tetrazole 97.5 parts of β-(phenylsulphonyl)-propionitrile are stirred together with 32 parts of sodium azide, 27 parts of ammonium chloride and 170 parts of dimethylformamide for 4 hours at 130°, and then further processed as in Example 2. Recrystallisation from methanol yields the tetrazole in the form of white crystals which melt at 136°–138°.

EXAMPLE 4 m-Phenylene-di(tetrazolyl-5-methyl)sulphone 22.7 parts of m-phenylene-di-(cyanomethyl)sulphone, obtained from benzene-disulphinic acid and chloroacetonitrile are stirred together with 11.5 parts of sodium azide and 9.4 parts of ammonium chloride in 100 parts of dimethylformamide for 12 hours at 130° C. The dimethylformamide is distilled off in vacuo, and the residue is dissolved in 200 parts of water, after the addition of 50% sodium hydroxide solution, and the solution is decolorised with animal charcoal. The product is precipitated at pH 3.0 by the addition of concentrated hydrochloric acid, and isolated by filtration. It melts at 260°.

EXAMPLE 5

Foaming of polycarbonate

A commercial granulated polycarbonate which contains 5% of glass fibres (Lexan FL 900, General Electric) and which has a viscosity number of 0.495 and a density of 1.2 g/ccm is dried for 2.5 hours in an oven at 120°. It is then premixed with 0.1% of butyl stearate for 20 minutes in order to ensure the adhesion of the blowing agent; it is then mixed, by being rotated, with 0.35% by weight of 5-(phenylsulphomethyl)-tetrazole, and the whole is mixed in a Rhönrad mixer for a further 20 minutes. The mixture is processed, in an injection moulding machine, into the form of rectangular plates having dimensions of 80 × 50 × 6 mm. The cylinder temperatures are 250°, 270° and 209°, with a nozzle temperature of 280°. The cooling time in the mould is 50 seconds. The moulding obtained has a viscosity number of 0.485 and a density of 0.85 g/cm³. It has a smooth surface and a foamed core having a fine homogeneous pore structure, and it shows no discoloration.

EXAMPLE 6

Foaming of a polyester

A commercial polybutyleneterephthalate (Crastin S 600, Ciba-Geigy AG) is ground in a mill to a particle size of 400 μm. It has a density of 1.31 g/cm³ and before processing is dried for 6 hours at 100° in a vacuum drying chamber. 50 g of the PBT powder is in each case then homogenised with 0.3 g of 5-(p-tolylsulphonyl-methyl)-tetrazole. 6 g of the mixture is placed into a cylindrical aluminium mould of 11 cm³ content closable by screwing, and the closed mould is put into a furnace at 340°. After a duration of 12 minutes — the foamed synthetic material attains in this time a maximum temperature of 320° — the mould is removed from the furnace and cooled with cold water. The specimens removed from the mould have a density of 0.48–0.50 g/cm³, a smooth surface and a foamed core having a fine and homogeneous pore structure. Compared with a comparative specimen without blowing agent, the foamed specimens display no change of colour.

EXAMPLE 7

Foaming of an aromatic polyether

A commercial polyphenylene oxide granulate (Noryl FN 215, General Electric) is ground in a mill to a particle size of 400 μm. It has a density of 1.06 g/cm³, and before processing it is dried for 3 hours at 100° in an air-circulation oven. There is then mixed in each case 50 g of the polyphenylene oxide powder with 0.3 g of 5-(methylsulphonyl-methyl)-tetrazole. 7.5 g of the mixture is subsequently foamed, as described in Example 6, in a mould of 11 cm³ content by 12 minutes' heating in a furnace at 340° (max. internal temperature 320°). The foamed specimen has a density of 0.58–0.71 g/cm³, a smooth surface and a foamed core having a fine and homogeneous pore structure. The employed tetrazole produces no change of colour.

I claim:

1. Process for foaming high melting thermoplastic polymeric materials by the addition of 0.05 to 5% by weight of a sulphonyltetrazole of the formula I

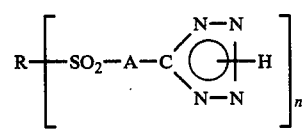

wherein
n is 1 or 2,
A represents an alkylene group which has 1–5 C atoms and which can be substituted by phenyl, and
R represents, if n is 1, alkyl having 1–4 C atoms, cyclohexyl, phenylalkyl having 7–8 C atoms, or an aryl group which has 6–10 C atoms and which can be substituted by alkyl having 1–2 C atoms, alkoxy having 1–2 C atoms, halogen, acylamino having 2–3 C atoms, carboxy or alkoxycarbonyl having 2–3 C atoms, and, if n is 2, represents phenylene, naphthylene or a radical of the formula II

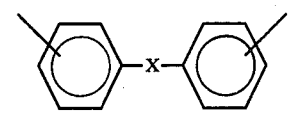

wherein X can be a direct bond, —O—, —S—, —SO₂—, —CH₂—, —C(CH₃)₂— or —NH—, to the thermoplastic material, and then heating the mixture.

2. Process according to claim 1, wherein the thermoplastic material is polypropylene, a styrene copolymer, a polycarbonate, an aromatic polyether, a polysulphone ether, a polyester or a polyamide, and foaming is performed at 230° to 300° C.

3. Process according to claim 1, in which there is used a sulphonyltetrazole of the formula I wherein R represents methyl, phenyl or tolyl, A represents —CH₂— or —CH₂CH₂—, and n is 1.

4. Process according to claim 1, in which there is used a compound of the formula I wherein n is 2, R represents phenylene, and A represents methylene.

5. Process according to claim 1, in which there is used a sulphonyltetrazole of the formula I wherein R represents methyl, A represents —CH₂—, and n is 1.

* * * * *